US007309686B2

(12) United States Patent
Birket

(10) Patent No.: US 7,309,686 B2
(45) Date of Patent: Dec. 18, 2007

(54) PROCESS FOR PRODUCING NATURAL SURFACTANTS AND COMPOSITIONS BASED ON NATURAL SURFACTANTS

(75) Inventor: Nigel Birket, Wellesbourne (GB)

(73) Assignee: ECO Holdings LLC, Miami, FL (US)

( * ) Notice: Subject to any disclaimer, the term of this patent is extended or adjusted under 35 U.S.C. 154(b) by 0 days.

(21) Appl. No.: 10/950,346

(22) Filed: Sep. 24, 2004

(65) Prior Publication Data

US 2005/0075260 A1   Apr. 7, 2005

Related U.S. Application Data

(60) Provisional application No. 60/508,340, filed on Oct. 3, 2003.

(51) Int. Cl.
*C11D 3/16* (2006.01)
*C11D 3/382* (2006.01)
*C11D 3/386* (2006.01)

(52) U.S. Cl. .................. 510/463; 71/23; 426/425; 426/431; 426/615; 426/655; 510/462; 510/499

(58) Field of Classification Search .............. 426/425, 426/431, 615, 655; 71/23, 11; 510/405, 510/462, 463, 467, 499
See application file for complete search history.

(56) References Cited

U.S. PATENT DOCUMENTS 2,446,091 A * 7/1948 Humm .................. 426/575
2,811,451 A * 10/1957 Tjoa ...................... 426/655
3,907,770 A * 9/1975 Strong ................... 536/114
4,125,392 A * 11/1978 Primo .................... 504/101
4,443,486 A * 4/1984 Guiseley ................ 426/584
5,801,240 A * 9/1998 Rideout et al. .......... 536/128
6,284,012 B1 * 9/2001 Mundschenk et al. ....... 71/23
2002/0025295 A1 * 2/2002 Kim ...................... 423/701
2003/0145395 A1 * 8/2003 Murakami ................ 8/405
2004/0115658 A1 * 6/2004 Weber et al. ............. 435/6
2005/0032663 A1 * 2/2005 Kim ...................... 510/350

FOREIGN PATENT DOCUMENTS

| CN | 1252954 | * | 5/2000 |
| JP | 04011871 | * | 1/1992 |
| JP | H04-11871 | * | 1/1992 |

OTHER PUBLICATIONS

Translation of CN 1252954; Hairen et al; May 17, 2000.*

* cited by examiner

*Primary Examiner*—Gregory R. Del Cotto
(74) *Attorney, Agent, or Firm*—Laurence A. Greenberg; Werner H. Stemer; Ralph E. Locher

(57) ABSTRACT

A process for extracting a natural surfactant includes the steps of providing a quantity of water, adding in a quantity of seaweed to the water resulting in a process medium, adding an enzyme solution to the process medium, and extracting the natural surfactant from the seaweed. The natural surfactant or kelp extract is then used in the formulation of many cleaning solutions.

29 Claims, No Drawings

US 7,309,686 B2

PROCESS FOR PRODUCING NATURAL SURFACTANTS AND COMPOSITIONS BASED ON NATURAL SURFACTANTS

CROSS-REFERENCE TO RELATED APPLICATIONS

This application claims the benefit under 35 U.S.C § 119(e) of provisional application No. 60/508,340, filed Oct. 3, 2003.

BACKGROUND OF THE INVENTION

FIELD OF THE INVENTION

The invention relates to a process that allows the production of a natural surfactant chemical, that has not previously been extracted from its natural source, and also to uses for the chemical in the formulation of cleaning products.

It is well known that some species of sea-weed, particularly those classified as "brown kelp" develop a coating on the surface of the fronds which gives the frond a slippery, soapy feel. However, there are no records of the chemical entities that constitute the surface being identified or extracted from the surface of the plant fronds.

Conventional processes used in the extraction of chemical compounds from sea-weed frequently make use of high temperatures and high pHs. These process conditions are detrimental to the stability of some chemical compounds produced by the sea-weed and in particular to a highly effective surfactant chemical with which certain species of seaweeds coat their fronds.

SUMMARY OF THE INVENTION

It is accordingly an object of the invention to provide a process for producing natural surfactants and compositions based on the natural surfactants that overcome the above-mentioned disadvantages of the prior art methods and compositions of this general type, which extracts and stabilizes a surfactant in a cost effective manner.

With the foregoing and other objects in view there is provided, in accordance with the invention, a process for extracting a natural surfactant. The process includes providing a quantity of water, adding in a quantity of seaweed to the water resulting in a process medium, adding an enzyme solution to the process medium, and extracting the natural surfactant from the seaweed.

An alternative to adding the enzyme is to create the enzyme by fermentation using naturally existing bacteria and the addition of cellulose, a carbohydrate or a sugar.

In accordance with an added mode of the invention, there are the steps of adding sodium chloride or other salt to the water for adjusting ionic strength; and setting an elevated water temperature to be between 12° C. and 60° C. Preferably the seaweed is kelp fronds from brown kelp and the kelp fronds are added to the water by a ratio range of 5:1 to 50:1 by weight. The pH of the process medium is adjusted to be between 4.0 and 8.5 on a daily basis. This can be done by introducing any acid, citric acid being an example, or any base, potassium hydroxide being an example, to the process medium.

Ideally the enzyme solution is hemicellulases, polysaccharidases, cellulases, pectinase, or alkaline proteinases. Between 5 and 20 grams of the enzyme solution is added for every 100 kg of process medium.

During the process the amount of dissolved solids in the process medium is measured preferably using a refractometer or a commercially available solids analysis device using heat or radiation. Other analytical methods can also used to measure the surfactant content. For example, an oven could be used to evaporate the liquid from the process medium and a scale is used to measure the weight of the remaining solids.

The process medium is ideally stirred continuously or at least two times a day for resuspending the kelp fronds. The process medium can be stirred by introducing a stream of compressed air, nitrogen or other gases into the bottom of a process tank for keeping the kelp fronds in suspension. Alternatively or additionally, the process medium is manually stirred or stirred with an automated mechanical device.

The process is terminated when a measured dissolved solids or surfactant content of the process medium becomes stable for 24 hours. The process medium is filtered using a sieve, cloth, or net of a mesh size sufficient to retain and separate the kelp fronds from a remaining process medium resulting in a separated process medium. Preferably the separated process medium is then passed through an ultra-filtration system.

Other features which are considered as characteristic for the invention are set forth in the appended claims.

Although the invention is described herein as embodied in a process for producing natural surfactants and compositions based on natural surfactants, it is nevertheless not intended to be limited to the details described, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments.

DESCRIPTION OF THE PREFERRED EMBODIMENTS

The process according to the invention enables a surfactant chemical to be released from the surface of sea-weed (kelp) fronds without its subsequent destruction. The process also prevents chemical deterioration of the surfactant after its extraction.

Preferably the kelp fronds are freshly cut and not allowed to dry as this causes deterioration of the surfactant chemical extracted from the kelp. Alternatively, the kelp may be air dried at the point of harvesting, or dried mechanically before being used in the process. Naturally, any form of kelp can be used but process efficiencies deteriorate with the less ideal conditions.

Ideally, whole kelp fronds are used in the process but, alternatively, cut, segmented, shredded, powdered or freeze-dried material may be used.

For the purposes and uses to which the kelp derived surfactant is to be used, it is essential that the process used to cause the release of the surfactant does not involve conditions that cause deterioration of the surfactant chemical. Such conditions may be described as, but are not confined to: high or low levels of pH, for example below a pH of 4 or above a pH of 12.5; or the application of heat above a temperature of 60° C.

It is also essential that the process conditions do not cause any damage to the kelp fronds that will cause the release of undesirable contaminants from the interstices of the fronds or from intracellular chemicals. Such conditions may be defined as, but are not confined to: pH levels below 4.5 or above pH 10.0; temperatures of above 60° C.; or severe agitation by any form, such as stirrer paddles or pumps, that may cause damage or bruising of the plant fronds.

Also, to prevent osmotic damage it is preferable that the process is carried out in conditions of salinity that is approximate to those of the water from which the kelp was harvested.

It is also essential that an agent, such as an enzyme, such as, but not confined to: hemicellulases; polysaccharidases; cellulases; pectinase; or alkaline proteinases; which are derived from a plant or microbial source, be present either through addition or creation by fermentation using naturally existing bacteria and the addition of cellulose, a carbohydrate or a sugar, to facilitate the release of the surfactant chemical. Without such a release agent the yield from the process becomes very low and concentration to a useable concentration is uneconomical.

In the general process, the kelp fronds are suspended in cold water to a concentration of between, but not confined to 2 kg to 20 kg of kelp per 100 kg of water, the salinity of which has been previously adjusted to be close to that of sea water by the addition of a salt such as sodium chloride. The pH of the process medium is then adjusted between a pH range, but not confined to a pH of 6.0 to 8.0.

The invention will now be described in the form of process examples.

EXAMPLE 1

A First Process Embodiment a). The salinity of an appropriate quantity of cold water, the temperature of which is maintained at a minimum of 12° C. and a maximum of 17° C. is adjusted by the addition of 35 grams/liter of a salt, for example but not limited to, sodium chloride.

b). The kelp fronds are added in a ratio of 10 kg of kelp to 100 kg of cold water.

c). The pH of the process mixture is then adjusted to between a minimum pH of 6.5 and a maximum of pH 8.5 either by the introduction of a solution of an acid such as citric acid (if the pH is too high) or by the introduction of a solution of a base such as potassium hydroxide (if the pH is too low). During the pH adjustment process the process medium is gently stirred, manually, by a paddle.

d). An enzyme solution containing the enzyme hemicellulase is added in the proportion of between 5 grams and 20 grams of the enzyme protein to 100 kg of process medium.

e). A measurement is made of the amount of dissolved solids in the water, using a refractometer or other suitable measuring system.

f). The process medium is stirred gently two to three times daily so as to re-suspend the kelp fronds.

g). The pH is adjusted, on a daily basis, to maintain a pH of between a minimum of 6.5 and a maximum of 8.5.

h). The process is terminated when the measured dissolved solids content of the process medium becomes stable for 24 hours. Normally the process will take between 3 and 5 days.

i). The process is stopped by filtering the process medium through a sieve, cloth, or net of a mesh size sufficient to retain and separate the kelp fronds from the remainder of the process medium.

j). Preferably, to obtain a useable concentration of the desired natural surfactant, the separated process medium is passed through an ultrafiltration system until the measured dissolved solids content reaches 10%.

k). The concentrated process medium is stabilized by adjusting the pH of the medium to between a minimum of pH 6.0 and a maximum of pH 8.0 by the addition of a solution of acid such as citric acid and the addition of a preservative such as potassium sorbate. The pH range chosen is that at which the natural surfactant is stable for a minimum of 2 years when kept at a temperature between 15° C. and 40° C.

EXAMPLE 2

A Second Process Embodiment a). The salinity of an appropriate quantity of cold water, the temperature of which is maintained at a minimum of 12° C. and a maximum of 17° C., is adjusted by the addition of 35 grams/liter of a salt such as sodium chloride.

b). The kelp fronds are then added in a ratio of 10 kg of kelp fronds to 100 kg of cold water.

c). The pH of the process mixture is then adjusted to between a minimum pH of 6.5 and a maximum pH of 8.5 either by the introduction of a solution of an acid such as citric acid (if the pH is too high) or by the introduction of a solution of a base such as potassium hydroxide (if the pH is too low). During the pH adjustment process, the process medium is gently stirred, manually, by a paddle.

d). An enzyme solution containing the enzyme cellulose, which must have a low activity, is added in the proportion of between 5 grams and 20 grams of the enzyme protein to 100 kg of process medium.

e). A measurement of the amount of dissolved solids, using a refractometer or other suitable measuring system.

f). The process medium is stirred gently by the introduction of a stream of nitrogen into the bottom of the process tank so that the kelp fronds are kept in suspension.

g). The pH is adjusted on a daily basis to maintain a pH of between 7.5 and 8.0.

h). The process is terminated when the measured dissolved solids content of the process medium reaches at least 3% or becomes stable for 24 hours, whichever is the first. Normally, the process will take between 3 and 5 days.

i). The process is stopped by filtering the process medium through a sieve, cloth, or net of a mesh size sufficient to retain and separate the kelp fronds from the remainder of the process medium.

j). Preferably, to obtain a useable concentration of the desired natural surfactant, the separated process medium is passed through an ultrafiltration system until the measured dissolved solids content reaches 10%.

k). The concentrated process medium is stabilized by adjusting the pH of the medium to between a minimum of pH 6.0 and a maximum of pH 8.0 by the addition of a solution of an acid such as citric acid and the addition of potassium sorbate to a concentration of 0.1%. The pH range chosen is that at which the natural surfactant is stable for a minimum of 2 years when kept at a temperature of between 15° C. and 40° C.

EXAMPLE 3

A Third Process Embodiment a). The salinity of an appropriate quantity of cold water, the temperature of which is maintained at a minimum of 12° C. and a maximum of 17° C., is adjusted by the addition of 35 grams/liter of a salt such as sodium chloride.

b). The kelp fronds are then added in a ratio of 10 kg of kelp fronds to 100 kg of cold water.

c). Heat in an appropriate form is applied to the tank jacket to raise the temperature of the process medium to 25° C.

d). The pH of the process mixture is then adjusted to between a pH of 7.5 and pH 8.0 either by the introduction of a solution of an acid such as citric acid (if the pH is too high) or by the introduction of a solution of a base such as potassium hydroxide (if the pH is too low). During the pH adjustment process the process medium is gently stirred, manually, by a paddle.

e). An enzyme solution containing the enzyme papain is added in the proportion of between 5 grams and 20 grams of the enzyme protein to 100 kg of process medium.

f). A measurement of the amount of dissolved solids, using a refractometer or other suitable measuring system.

g). The process medium is stirred gently by the introduction of a stream of nitrogen into the bottom of the process tank so that the kelp fronds are kept in suspension.

h). The pH is adjusted on a daily basis to maintain a pH of between 7.5 and 8.0.

i). The process is terminated when the measured dissolved solids content of the process medium reaches at least 2% or becomes stable for 24 hours, whichever is the first. Normally, this process will take between 3 and 5 days.

j). The process is stopped by filtering the process medium through a sieve, cloth, or net of a mesh size sufficient to retain and separate the kelp fronds from the remainder of the process medium.

k). Preferably, to obtain a useable concentration of the desired surfactant, the separated process medium is passed through an ultrafiltration system until the measured dissolved solids content reaches 10%.

l). The concentrated process medium is stabilized by adjusting the pH of the medium to between a minimum of pH 6.0 and a maximum of pH 8.0 by the addition of a solution of an acid such as citric acid and the addition of potassium sorbate to a concentration of 0.1%. The pH range chosen is that at which the natural surfactant is stable for a minimum of 2 years when kept at a temperature of between 15° C. and 40° C.

It is noted that any acid or base may be used for controlling the pH values and the acids and bases mentioned are only exemplary.

The invention now turns to using the surfactant (kelp extract), in various cleaning based products.

Product 1 - All Purpose Cleaner and Degreaser

| Raw Materials | Typical composition % by weight | Range % by weight |
| --- | --- | --- |
| Water | 79.5 | 60.0-95.0 |
| di-basic salt (e.g. sodium carbonate) | 3.0 | 1.0-10.0 |
| Non-ionic & Amphoteric Surfactants | 15.0 | 3.0-30.0 |
| Kelp Extract | 2.5 | 0.5-10.0 |
| Preservative (e.g. Potassium Sorbate) | q.s. | q.s. |
| Total | 100.0 | 100.00 | q.s. = quantity sufficient.

Instructions:
a). Add the di-basic salt to the water and mix until dissolved.
b). Add the remaining ingredients in the order given.

Product 2 - Carpet Extraction Cleaner

| Raw Material | Typical composition % by weight | Range % by weight |
| --- | --- | --- |
| Water | 89.0 | 60.0-95.0 |
| Buffering Salt (e.g. Sodium Carbonate) | 2.0 | 0.5-10.0 |
| Builder (e.g. Sodium Tripolyphosphate) | 4.5 | 1.0-15.0 |
| Non-Ionic Surfactant | 1.5 | 0.0-6.0 |
| Kelp Extract | 1.0 | 0.5-3.0 |
| Fatty Acid esters (e.g. Estasol) | 2.0 | 0.0-7.0 |
| Total | 100.0 | 100.0 |

Instructions:
a). Add the buffering salt and builder to the water and mix until dissolved.
b). Add the remaining ingredients in the order given.

Product 3 - High Performance Cleaner

| Raw Material | Typical composition % by weight | Range % by weight |
| --- | --- | --- |
| Water | 81.1 | 40.0-95.0 |
| Buffering Salt (e.g. Sodium Carbonate) | 1.5 | 0.25-7.0 |
| Non-Ionic & Amphoteric Surfactants | 10.0 | 1.5-30.0 |
| Kelp Extract | 2.5 | 0.25-6.0 |
| Triethanolamine | 0.5 | 0.0-5.0 |
| Builder | 0.2 | 0.0-10.0 |
| Fatty Acid Esters (e.g. Estasol) | 1.5 | 0.0-10.0 |
| Short Chain Esters | 2.0 | 0.0-10.0 |
| Plant Terpenes (e.g. Dipentene) | 0.7 | 0.0-10.0 |
| Total | 100.0 | 100.0 |

Instructions:
a). Add the buffering salt to the water and mix until dissolved.
b). Add the remaining ingredients in the order given.

I claim:

1. A process for extracting a natural surfactant, which comprises the steps of:
   providing a quantity of water;
   adding in a quantity of seaweed to the water resulting in a process medium;
   adjusting a pH of the process medium to be between 6.0 and 8.0;
   adding an enzyme solution to the process medium;
   maintaining a temperature of the process medium to not exceed 60° C. during the entire process; and
   extracting the natural surfactant from the seaweed.

2. A process for extracting a natural surfactant, which comprises the steps of:
   providing a quantity of water;
   adding salt to the water for adjusting ionic strength;
   setting a water temperature to be between 12° C. and 60° C.;

adding in a quantity of seaweed to the water resulting in a process medium and maintaining a temperature of the process medium to not exceed 60° C. during the entire process;

adjusting a pH of the process medium to be between 4.5 and 8.5;

adding an enzyme solution to the process medium; and extracting the natural surfactant from the seaweed.

3. The process according to claim 1, which further comprises:

using kelp fronds from brown kelp as the seaweed; and adding the kelp fronds to the water by a ratio range of 1:5 to 1:50 by weight.

4. The process according to claim 1, which further comprises:

manually stirring the process medium.

5. The process according to claim 1, which further comprises introducing a compound selected from the group consisting of bases and acids to the process medium for adjusting the pH.

6. The process according to claim 1, which further comprises forming the enzyme solution from hemicellulase.

7. The process according to claim 6, which further comprises adding between 5 and 20 grams of the hemicellulase for every 100 kg of the process medium.

8. A process for extracting a natural surfactant, which comprises the steps of:

providing a quantity of water;

setting a water temperature to be between 12° C. and 17° C.;

adding in a quantity of seaweed to the water resulting in a process medium maintaining a temperature of the process medium to not exceed 60° C. during the entire process; adjusting a pH of the process medium to be between 4.5 and 8.5;

adding an enzyme solution to the process medium;

measuring an amount of dissolved solids in the process medium; and extracting the natural surfactant from the seaweed.

9. The process according to claim 8, which further comprises measuring the amount of the dissolved solids with a refractometer or a solids analysis device.

10. The process according to claim 3, which further comprises stirring the process medium at least two times a day for resuspending the kelp fronds.

11. A process for extracting a natural surfactant, which comprises the steps of:

providing a quantity of water;

adding in a quantity of seaweed to the water resulting in a process medium;

adjusting a pH of the process medium to be between 6.5 and 8.5;

adding an enzyme solution to the process medium;

maintaining a temperature of the process medium to not exceed 60° C. during the entire process;

terminating the process when a measured dissolved solids content of the process medium becomes stable for 24 hours or a surfactant concentration becomes stable for a 24 hour period; and extracting the natural surfactant from the seaweed.

12. The process according to claim 3, which further comprises filtering the process medium through one of a sieve, cloth, and net of a mesh size sufficient to retain and separate the kelp fronds from a remaining process medium resulting in a separated process medium.

13. The process according to claim 12, which further comprises passing the separated process medium through an ultrafiltration system until a measured dissolved solids content reaches 10%.

14. The process according to claim 1, which further comprises adjusting the pH of the process medium by adding a solution of acid and preservative to a concentration of 0.1%.

15. The process according to claim 1, which further comprises forming the enzyme solution from cellulose.

16. The process according to claim 15, which further comprises adding between 5 and 20 grams of the cellulose for every 100 kg of the process medium.

17. The process according to claim 3, which further comprises stirring the process medium by introducing a stream of nitrogen into a bottom of a process tank for keeping the kelp fronds in suspension.

18. The process according to claim 1, which further comprises adjusting the pH of the process medium, on a daily basis.

19. A process for extracting a natural surfactant, which comprises the steps of:

providing a quantity of water;

adding in a quantity of seaweed to the water resulting in a process medium;

raising a temperature of the process medium up to 17° C. and not letting the temperature to exceed 60° C. for the entire process adjusting a pH of the process medium to be between 4.5 and 8.5;

adding an enzyme solution to the process medium; and extracting the natural surfactant from the seaweed.

20. The process according to claim 1, which further comprises forming the enzyme solution from papain.

21. The process according to claim 20, which further comprises adding between 5 and 20 grams of the papain for every 100 kg of the process medium.

22. The process according to claim 1, which further comprises terminating the process when a measured dissolved solids content of the process medium becomes stable for 24 hours.

23. The process according to claim 1, which further comprises filtering the process medium for separating the natural surfactant from the seaweed.

24. The process according to claim 2, which further comprises using sodium chloride as the salt.

25. The process according to claim 5, which further comprises:

using citric acid as the acid; and using potassium hydroxide as the base.

26. The process according to claim 1, wherein the step of adding the enzyme solution step includes the steps of:

creating the enzyme solution by fermentation using naturally existing bacteria in the process medium and an addition of cellulose, a carbohydrate or sugar.

27. The process according to claim 1, which further comprises selecting the enzyme solution from the group consisting of hernicellulases, polyssocharidases, cellulases, pectinase, and alkaline proteinases.

28. The process according to claim 14, which further comprises:
  using citric acid as the acid; and
  using potassium sorbate as the preservative.

29. A process for extracting a natural surfactant, which comprises the steps of:
  providing a quantity of water;
  adding salt to the water for adjusting salinity;
  adding in a quantity of kelp fronds to the water resulting in a process medium;
  adjusting a pH of the process medium to be between 6.5 and 8.5;
  having an enzyme solution present with an enzyme selected from the group consisting of hemicellulases, polysaccharidases, cellulases, pectinase, or alkaline proteinases;
  maintaining a temperature of the process medium to not exceed 60° C. during the entire process; and
  filtering the process medium for separating the natural surfactant from the kelp fronds.

* * * * *